(12) United States Patent
Cheng

(10) Patent No.: US 8,788,005 B1
(45) Date of Patent: Jul. 22, 2014

(54) SYSTEM AND METHOD FOR NON-INVASIVE MONITORING OF CEREBRAL TISSUE HEMODYNAMICS

(71) Applicant: Mespere Lifesciences Inc., Waterloo (CA)

(72) Inventor: Xuefeng Cheng, Waterloo (CA)

(73) Assignee: Mespere Lifesciences Inc., Waterloo, Ontario (CA)

( * ) Notice: Subject to any disclaimer, the term of this patent is extended or adjusted under 35 U.S.C. 154(b) by 0 days.

(21) Appl. No.: 13/913,911

(22) Filed: Jun. 10, 2013

Related U.S. Application Data

(63) Continuation-in-part of application No. 12/713,368, filed on Feb. 26, 2010, now Pat. No. 8,463,348.

(60) Provisional application No. 61/202,441, filed on Feb. 27, 2009.

(51) Int. Cl.
*A61B 5/00* (2006.01)

(52) U.S. Cl.
USPC .......................................................... 600/324

(58) Field of Classification Search
USPC .......................................................... 600/324
See application file for complete search history.

(56) References Cited

U.S. PATENT DOCUMENTS

| 7,725,187 B1 * | 5/2010 | Nabutovsky et al. ............ 607/19 |
| 7,738,935 B1 * | 6/2010 | Turcott .......................... 600/336 |
| 2010/0198027 A1 * | 8/2010 | Dixon ........................... 600/323 |

FOREIGN PATENT DOCUMENTS

WO    WO 2008098353 A1 *  8/2008  ............. A61B 5/021

* cited by examiner

*Primary Examiner* — Clayton E LaBalle
*Assistant Examiner* — Fang-Chi Chang

(57) ABSTRACT

A method and system are provided which are useful for the non-invasive determination and monitoring of cerebral blood oxygenation in a patient. The system comprises a first module for optically generating at least first and second internal jugular venous output signals against time at at least first and second wavelengths of light; and a second module for generating first and second cardiac arterial output signals at the first and second wavelengths of light, respectively. The system may additionally include a third module for optically generating at least first and second external jugular venous output signals against time at at least first and second wavelengths of light, and one or more cerebral modules for optically generating at least first and second local cerebral output signals against time at at least first and second wavelengths of light. The system includes a signal processing means adapted to calculate average cerebral, arterial, venous scalp and local cerebral blood oxygenation values based on the output from each of the modules.

12 Claims, 9 Drawing Sheets

SYSTEM AND METHOD FOR NON-INVASIVE MONITORING OF CEREBRAL TISSUE HEMODYNAMICS

This application is a continuation-in-part application of U.S. Ser. No. 12/713,368 filed Feb. 26, 2010 which claims the benefit of U.S. Provisional Application No. 61/202,441, filed Feb. 27, 2009, and incorporates such provisional application in its entirety by reference.

FIELD OF THE INVENTION

The present invention is related to techniques for monitoring vital functions of the human body, including cerebral tissue hemodynamics. It relates, in particular, to an optical method and system for the non-invasive and continuous monitoring of cerebral parameters such as cerebral tissue oxygenation.

BACKGROUND OF THE INVENTION

Monitoring cerebral tissue oxygenation or oxygen consumption is critical for the management of patients with traumatic brain injury and patients undergoing cardiac by-pass surgeries. Insufficient cerebral tissue oxygen consumption over a few minutes can lead to irreversible, severe, neurological damage. Cerebral oxygen consumption can be estimated through the differences between arterial and cerebral venous blood oxygen saturation. Pulse Oximetry (such as Masimo Radical-7™) is the clinical standard for non-invasive monitoring of arterial blood oxygen saturation at the finger tip. However, the determination of cerebral venous blood saturation is conducted using highly invasive venous catheters such as the jugular vein bulb catheter. Non-invasive methods such as pulse oximtery cannot be used to obtain cerebral venous blood oxygenation because, unlike arterial vessels, venous blood vessels are passive and without pulsation.

Cerebral tissue oximetry has also been developed based on near infrared spectroscopy to non-invasively measure tissue oxygenation at various sites on the head (such as INVOS Cerebral Oximeter of Somanetics Inc.). However, it is difficult for light to penetrate through the skull and reach cerebral tissues. As a result, the device is limited to measuring only a small spot on the surface of the cortical tissue which does not necessarily represent the overall cerebral tissue oxygenation, e.g. especially tissues deep inside brain.

Accordingly, there is a need to develop a means to accurately and non-invasively determine cerebral tissue dynamics.

SUMMARY OF THE INVENTION

The present invention provides a novel method of determining cerebral tissue oxygenation, as well as a system useful for such a determination. The method includes optically obtaining an output signal of internal jugular venous blood at at least two different wavelengths, separating from these output signals the cardiac arterial pulse portion of the signal to provide an output signal of cerebral venous blood at the selected wavelengths, and determining the cerebral tissue oxygenation based on the cerebral venous output signals.

Thus, in one aspect of the invention, a method for determining cerebral tissue oxygenation in a patient is provided comprising the steps of:

1) generating at least first and second jugular venous output signals against time based on the reflection of first and second wavelengths of light, respectively, from an external tissue site on the patient in the proximity of the internal jugular vein;

2) obtaining corresponding first and second cardiac arterial output signals using a pulse oximeter for the first and second wavelengths of light, respectively, from the patient, and 3) determining average cerebral tissue oxygenation based on the first and second cerebral venous output signals, and arterial tissue oxygenation based on the first and second cardiac arterial output signals with a processor.

In another aspect of the invention, a method is provided comprising the steps of:

1) determining scalp venous blood oxygenation by generating at least first and second output signals of change in blood volume as current or voltage over time using at least one photodetector based on the reflection or transmission of at least first and second wavelengths of light from at least one light source, wherein the light is applied to the neck of the patient in the proximity of the external jugular vein;

2) determining the average cerebral venous oxygenation by generating at least first and second output signals of change in blood volume as current or voltage over time using at least one photodetector based on the reflection or transmission of at least first and second wavelengths of light from at least one light source, wherein the light is applied to the neck of the patient in the proximity of the internal jugular vein;

3) determining local cerebral blood oxygenation at one or more cerebral sites by generating at least first and second output signals of change in blood volume as current or voltage over time using at least one photodetector based on the reflection or transmission of at least first and second wavelengths of light from at least one light source, wherein the light is applied to the head of the patient in the proximity of the one or more cerebral sites;

4) determining cerebral arterial blood oxygenation by generating at least first and second cardiac arterial output signals over time using a pulse oximeter for the first and second wavelengths of light; and 5) comparing the local cerebral blood oxygenation to the average cerebral blood oxygenation, scalp venous blood oxygenation and scalp arterial oxygenation using a processor to identify changes in one or more of these and thereby detect cerebral ischemia.

In another aspect, a system useful to determine and monitor cerebral tissue oxygenation in a patient is provided comprising:

1) a first module for optically generating first and second jugular venous output signals against time at first and second wavelengths of light, respectively, from the patient;

2) a second module for generating first and second cardiac arterial output signals at the first and second wavelengths of light, respectively, from the patient; and 3) a signal processing means adapted to calculate average cerebral tissue oxygenation based on the first and second cerebral venous output signals, and arterial tissue oxygenation based on the first and second cardiac arterial output signals.

These and other aspects of the present invention will become apparent by reference to the detailed description that follows, and the drawings in which:

DETAILED DESCRIPTION OF THE INVENTION

Figure 1:
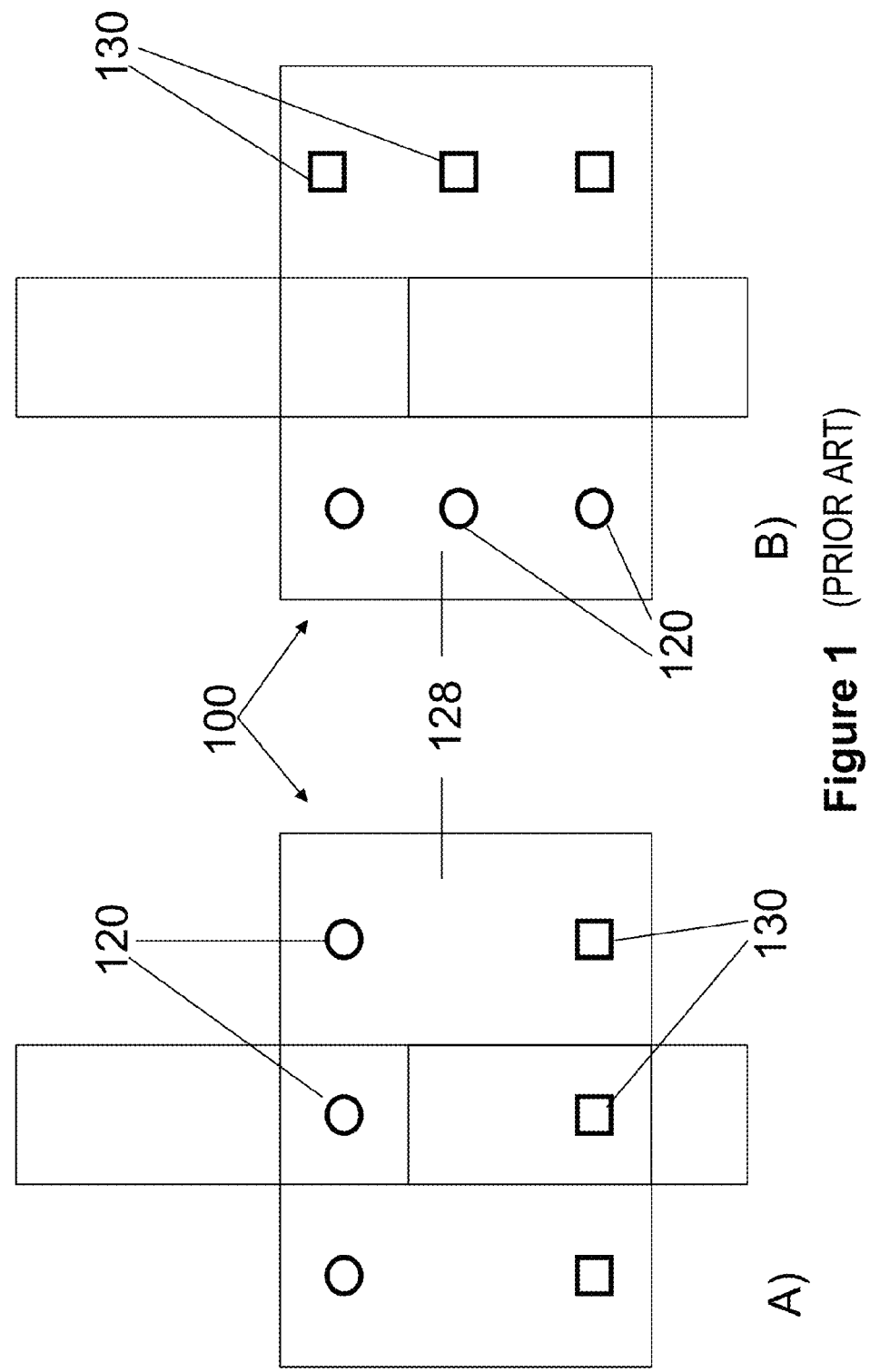
FIG. 1 illustrates a top view of an embodiment of a device useful to obtain a jugular venous output signal.

An optical method for determining cerebral tissue oxygenation in a patient is provided. The method includes optically generating at least first and second jugular venous output signals against time based on the reflection of at least first and second wavelengths of light from an external tissue site on the patient in the proximity of the internal jugular vein. Cardiac arterial output signals at the first and second wavelengths are also obtained from the patient and subtracted from the first and second jugular venous output signals to generate first and second cerebral venous output signals from which cerebral tissue oxygenation is calculated.

The invention utilizes the fact that the internal jugular vein contains cerebral venous blood returning to the right atrium of the heart. An internal jugular venous output signal can be determined within the internal jugular vein by measuring light reflected from an external tissue site on a patient in the proximity of the internal jugular vein. However, the signal obtained from the jugular vein will also incorporate a cardiac arterial output signal, e.g. from the carotid artery (due to the close proximity of the internal jugular vein and carotid artery). Accordingly, the portion of the signal due to carotid artery pulsation is determined and subtracted from the jugular vein signal to obtain a cerebral venous output signal from which cerebral tissue oxygenation may be calculated using, for example, modified Beer Lambert's law, as will be described.

The term "output signal" as it is used herein with respect to jugular venous output signals, cardiac arterial output signals and cerebral venous output signals, refers to a current/voltage signal which corresponds to the optical signal obtained as a result of the pulse in each of the internal jugular vein, the carotid artery and the cerebral veins (determined by removing the cardiac arterial optical signal from the jugular venous optical signal), respectively.

In a first step of the method, jugular venous output signals against time are optically obtained by directing light of at least two different wavelengths, e.g. a first wavelength and a second wavelength, each in the range of 400 nm to 1000 nm, to an external tissue site on a patient that is in the proximity of the internal jugular vein, detecting light reflected from the tissue site in each case, e.g. from the first and second wavelengths, including light transmitted through the tissue site, and translating the detected light into a first and second jugular vein output signals against time. For the determination of cerebral tissue oxygenation, for example, first and second wavelengths of light are selected between 400 and 1000 nm. In one embodiment, the selected wavelengths of light may be 690 nm, for deoxygenated haemoglobin content, and 830 nm, for oxygenated haemoglobin content. As one of skill in the art will appreciate, more than two wavelengths of light may be utilized in this method. The use of more than two wavelengths may provide a more accurate result, e.g. reduce error. An example of a device useful to obtain such first and second jugular vein output signals will be described.

In a second step of the method, in order to exclude extraneous cardiac arterial output, e.g. such as from the carotid artery, from the jugular vein output signals obtained, the cardiac arterial output signal of the patient is determined at each wavelength and translated into an arterial output signal against time. Cardiac arterial output in a patient may be determined using well-established techniques, including for example, pulse oximetry in which arterial pulse is optically determined in a patient and translated into a cardiac arterial output signal.

Once a cardiac arterial output signal is obtained at each of the selected wavelengths, e.g. first and second wavelengths, it is separated or removed from each of the first and second jugular venous output signals, respectively, to generate first and second cerebral venous output signals. This separation of the cardiac arterial output signal from the first and second jugular venous output signals is generally effected digitally, using a digital signal processor, as will be described, incorporating an appropriate algorithm for this purpose.

Cerebral tissue oxygenation may then be calculated based on the first and second cerebral venous output signals using modified Beer Lambert's law as follows:

Modified Beer Lambert's Law

The first cerebral venous pulse signal (e.g. current) may be expressed as:

$$I_{\lambda_1} = I_{0,\lambda_1} e^{-B[\varepsilon_{Hb,\lambda_1} \cdot (C_{Hb} + \Delta C_{Hb}) + \varepsilon_{HbO,\lambda_1} \cdot (C_{HbO} + \Delta C_{HbO})]L + A} \quad (1)$$

where:

$I_{\lambda_1}$ is the output signal obtained at a first wavelength of light $\lambda_1$, $I_{0\times\lambda_1}$ is the signal from the light source at the first wavelength $\lambda_1$, $C_{Hb}, C_{HbO}$ are the concentrations of deoxygenated and oxygenated haemoglobin, respectively, of steady tissue medium blood;

$\Delta C_{Hb}, \Delta C_{HbO}$ are the changes in the concentrations of deoxygenated and oxygenated haemoglobin, respectively, derived from measured values as shown in equations 2-4 which follow;

$\varepsilon_{Hb,\lambda_1}, \varepsilon_{HbO,\lambda_1}$ are the absorption properties of deoxygenated and oxygenated haemoglobin, respectively, at the first wavelength $\lambda_1$ for the purposes of calculating blood oxygen saturation. Blood saturation of other chromophores can also be calculated by substituting into the equation the appropriate extinction coefficients ($\varepsilon$) for the selected chromophore including, for example, water, cytochromes such as cytochrome oxides, and cholesterol; and A. B are constants determined by boundary conditions.

The relative change in signal from the signal emitted by a light source to the detected signal is represented for a first wavelength by:

$$\Delta I_{\lambda_1} = e^{-B[\varepsilon_{Hb,\lambda_1} \cdot (\Delta C_{Hb}) + \varepsilon_{HbO,\lambda_1} \cdot (\Delta C_{HbO})]L}; \quad (2)$$

or as $$OD_{\lambda_1} = \ln(\Delta I_{\lambda_1}) = -B(\varepsilon_{Hb,\lambda_1} \cdot \Delta C_{Hb} + \varepsilon_{HbO,\lambda_1} \cdot \Delta C_{HbO}) \quad (3).$$

Similarly, the change in signal between emitted and detected signal for a second light wavelength is represented by:

$$OD_{\lambda_2} = \ln(\Delta I_{\lambda_2}) = -B(\varepsilon_{Hb,\lambda_2} \cdot \Delta C_{Hb} + \varepsilon HbO,\lambda_2 \cdot \Delta C_{HbO}) \quad (4)$$

Cerebral blood oxygenation derived from the cerebral venous output signal is then determined using the following equation:

$$S_{jv}O_2 = \frac{\Delta C_{HbO}}{\Delta C_{Hb} + \Delta C_{HbO}} \quad (5)$$
$$= \frac{\varepsilon_{Hb,\lambda_1} \cdot OD_{\lambda_2} - \varepsilon_{Hb,\lambda_2} \cdot OD_{\lambda_1}}{(\varepsilon_{Hb,\lambda_1} - \varepsilon_{HbO,\lambda_1}) \cdot OD_{\lambda_2} - (\varepsilon_{Hb,\lambda_2} - \varepsilon_{HbO,\lambda_2}) \cdot OD_{\lambda_1}}.$$

Alternatively, cerebral oxygenation based on internal jugular venous output and cardiac arterial oxygenation based on cardiac arterial output are each determined and cerebral oxygenation consumption is estimated by the difference of cardiac arterial oxygenation and internal jugular venous oxygenation.

A device 100 useful to obtain the first and second output signals of the internal jugular vein is shown in FIG. 1, and as described in WO 2008/098353 A1. The device comprises at least two light-emitting components 120, each emitting light of a different wavelength within the range of 400 nm to 1000 nm. The device also comprises a light-receiving component 130 for each light-emitting component 120 adapted to receive the emitted or reflected light at a given wavelength.

The light emitting component (e.g. light source 120 or transmitting optical fibres 124) and light receiving component (e.g. photodetector 130 or receiving optical fibres 126) are set in a patch probe 128, and may be arranged as shown in FIG. 1; however, as one of skill in the art will appreciate, alternative arrangements of the light-emitting components and light-receiving components exist which will not affect the function of the device 100. For example, the device 100 may comprise multiple patch probes 128, each of which includes a light-emitting component and a light-receiving component. Alternatively, the device 100 may comprise a single patch 128 including multiple light-emitting components and light-receiving components. In another alternative, the device 100 may comprise a first patch 128 with one or more light-emitting components and light-receiving components, and a second patch with one or more light-emitting components and corresponding light-receiving components.

Figure 2:
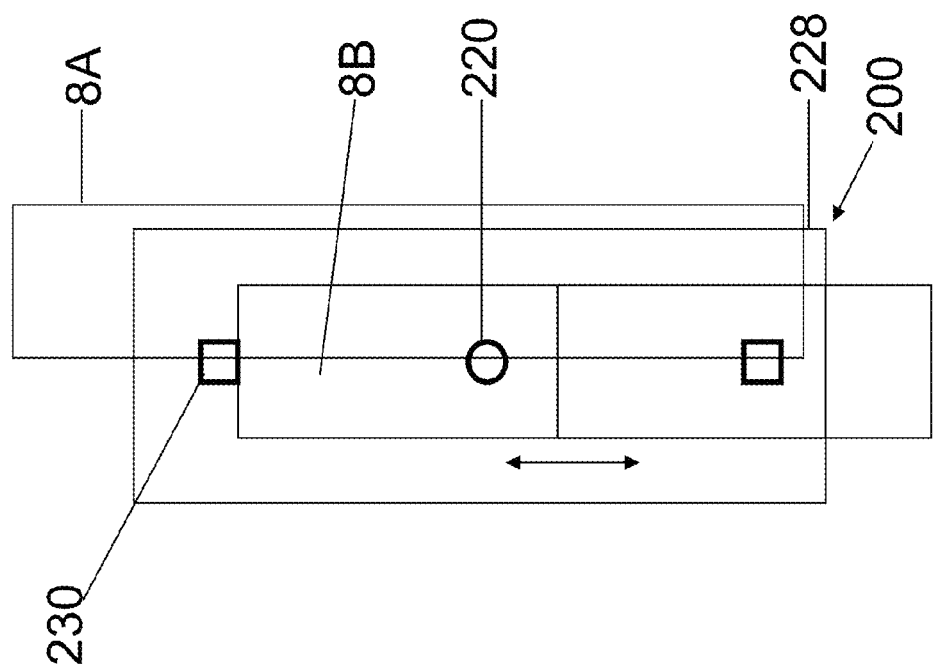
FIG. 2 is a top view of another embodiment of the device of FIG. 1.
Figure 3:
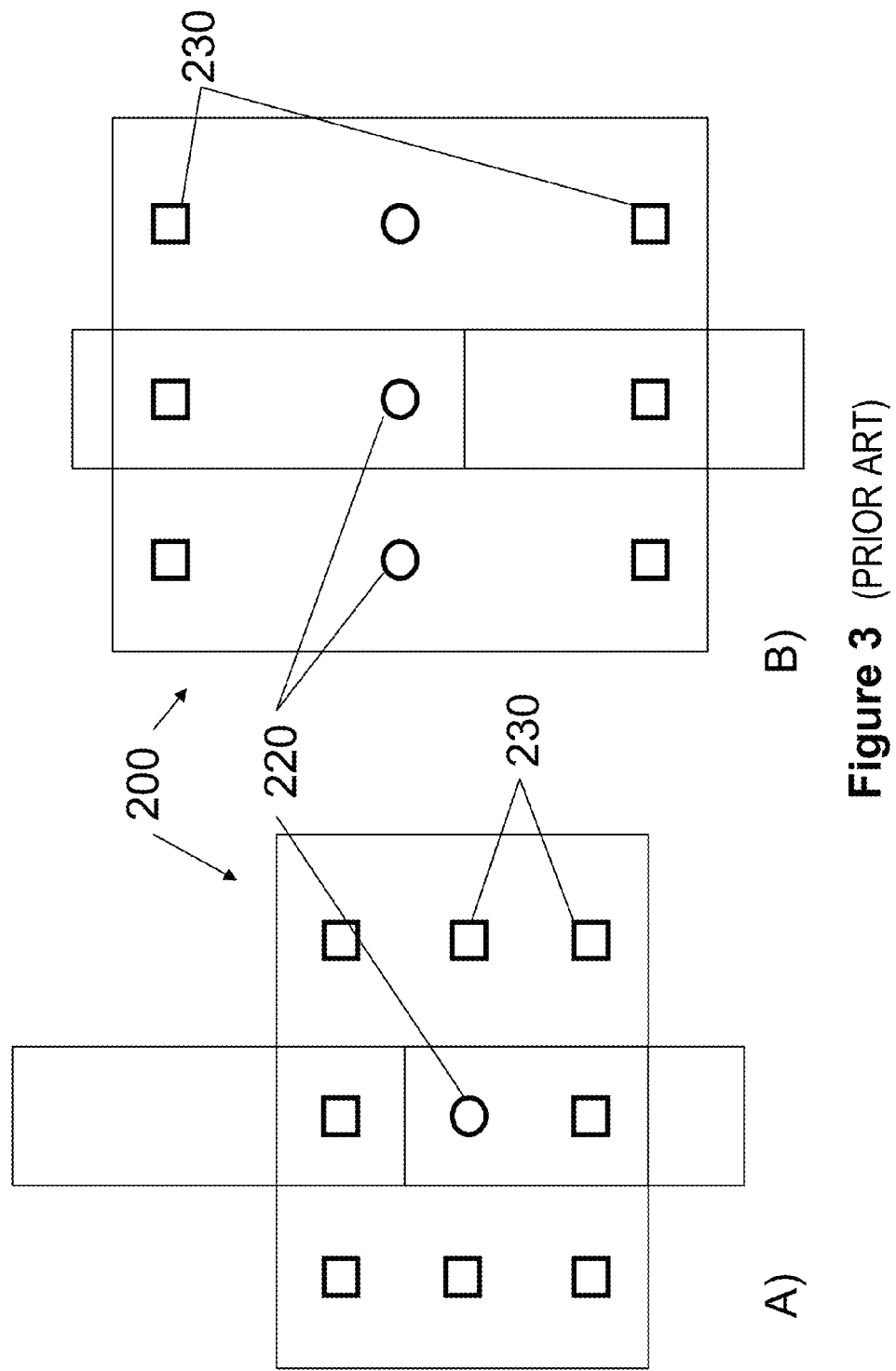
FIG. 3 is a top view of further embodiments of the device of FIG. 1.

In another embodiment, illustrated in FIGS. 2 and 3, a device 200 is provided comprising one or more light sources 220, each emitting selected wavelengths of light in the 400 nm to 1000 nm range. Each light source 220 is coupled with at least two photodetectors 230 each adapted to receive light emitted at a given frequency. The device 200 is useful to simultaneously measure multiple cardiac blood vessel pulses, such as jugular venous pulse as well as carotid arterial pulse. As one of skill in the art will appreciate, in the case of multiple light sources 220, each light source is turned on in sequence, and the amplitude of light emitted from the light source(s) is modulated at a selected frequency, such as 10 kHz or 20 kHz. Alternatively, light emitted by a single light source 220 can be sequentially modulated at two alternating frequencies, such as 10 kHz and 20 kHz. The output from the photodetectors (e.g. current/voltage) is filtered at a frequency selected to correlate with a given frequency emitted from a light source, for example, using a band pass filter which allows a selected frequency, such as a 10 kHz or 20 kHz signal, to pass through but blocks other frequency components in the signal.

Each light source 120/220 may be any suitable light source such as a laser diode (e.g. RLT7605G, 760 nm, 5 mW, sm, 9.0 mmh, or RLT8510MG, 850 nm, 10 mW, sm, 5.6 mm), a light emitting diode (LED) or a broadband light source emitting a selected wavelength in the range of 400 nm to 1000 nm, for example, a wavelength in the range of 780 nm and 850 nm. In an embodiment, a single light source is adapted to emit light in two or more wavelengths, e.g. by association with a frequency oscillator. The light source 120/220 is powered by an appropriate power supply 118 such as a 12V DC power supply. Light from the light source 120/220 is directed to at least one external tissue site on the patient that is within close proximity to the internal jugular vein. Thus, the neck, for example, represents a suitable site for placement of the patch probe.

Light from the light source 120/220 may be directed or focussed by an optical lens into a transmitting means, such as transmitting optical fibre bundles, for transmission to the selected patient site. Receiving means, such as optical fibre bundles, may also be used to receive light that is reflected/transmitted from the patient site and convey this light to a photodetector 130/230. As one of skill in the art will appreciate, each fibre optic bundle will incorporate fibres manufactured of material appropriate for the transmission of the wavelength of the light emitted from the light source 120/220. For example, if the light source 120/220 emits in the visible wavelength range, both multiple mode plastic and glass optical fibres may be used. The number and diameter of the fibres in the fibre optic bundle is optimized empirically to provide the highest signal to noise ratio in a given application. The transmitting and receiving optical fibre bundles are set in the patch probe, either at distinct spaced sites or they may be combined together at a single site. Optical mirrors may be utilized to direct or reflect light from the transmitting fibre bundle into the tissue at the selected patient site, and to direct reflected or transmitted light from the patient site into a receiving fibre bundle.

It will also be appreciated that a combination of the foregoing embodiments may be utilized in the device. For example, the light source 120/220 may be set directly in the probe 128/228 to deliver light to the patient site, while the reflected/transmitted light is received by optical fibres for delivery to the photodetector 130/230. A converse embodiment may also be used in which the probe 128/228 comprises transmitting optical fibres to deliver light from the light source to the patient site, and a photodetector 130/230 set directly in the probe to receive the reflected/transmitted light. Accordingly, the light source 120/220 and photodetector 130/230 are each coupled to the probe (e.g. attached to, integrally formed with or set directly in the probe).

The distance between the component delivering light to the patient site (light source or transmitting optical fibres) and the component receiving light from the patient site (photodetector or receiving optical fibres) may vary depending on the nature of each of the components, while a typical distance is generally between 2 and 4 cm, for example, 3 cm.

The patch probe 128/228 may be made out of any material suitable to support the electronic/optical components it houses, e.g. light source, photodetector, optical fibres or mirrors, and which is compatible for placement on the skin. An example of one such suitable material is medical rubber. The patch may be held in position manually, may be held in position by adhesives (one side of the patch may be coated with a material that is adhesive to skin such as a hydro gel adhesive) or may be adapted to be held in place with straps that can be tied or otherwise secured. Opposing ends of the band may also include an adhesive material such as Velcro to facilitate their attachment and to hold the device in place.

The photodetector 130/230 translates received reflected/transmitted light into a recordable output such as current or voltage. An example of a suitable photodetector for use in the present device is a silicon photo diode (e.g. Hamamatsu S8553). Condensor lenses may be incorporated, if required, to refocus the reflected or transmitted beam of light to be received by the photodetector. As will be understood by a person skilled in the art, silicon photodiodes are semiconductor light sensors that generate a current or voltage when the P-N junction in the semiconductor is illuminated by light. Accordingly, the photodetector provides a current/voltage signal in response to the received light signal. Thus, the current/voltage signal output generated by the photodetector is proportional to the instantaneous light intensity of the light signal received at the photodetector. Accordingly, the photodetector provides a time-varying output (e.g. current/voltage as a function of time) which is dependent upon the received light and its characteristics.

Figure 4:
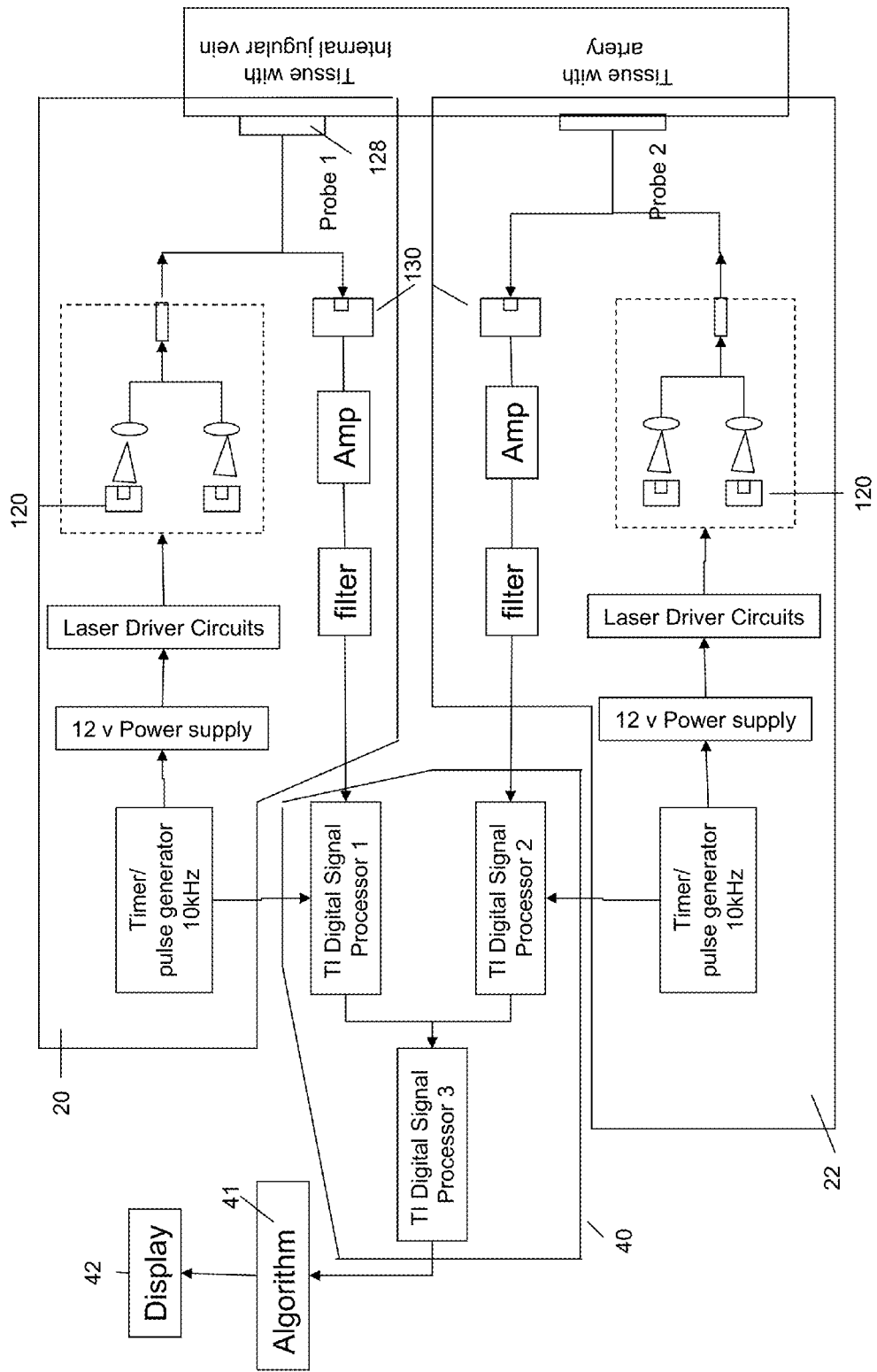
FIG. 4 is a block diagram illustrating a system according to an aspect of the invention.
Figure 5:
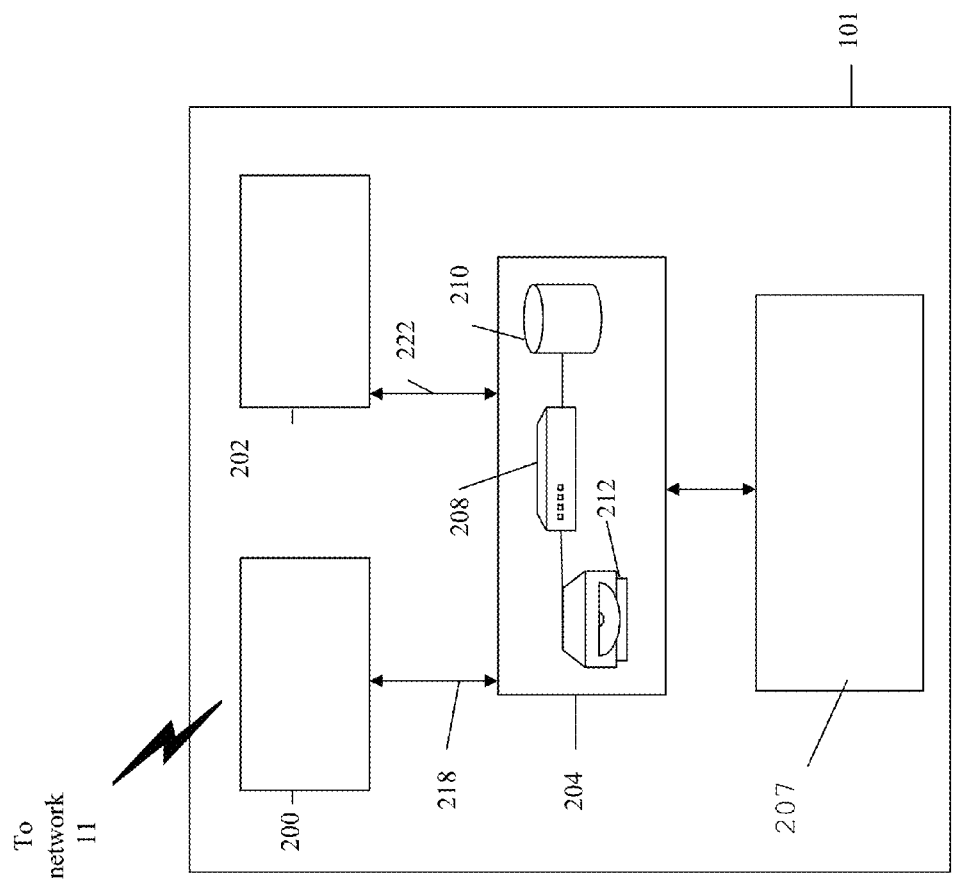
FIG. 5 is a block diagram also illustrating a system according to the invention.
Figure 6:
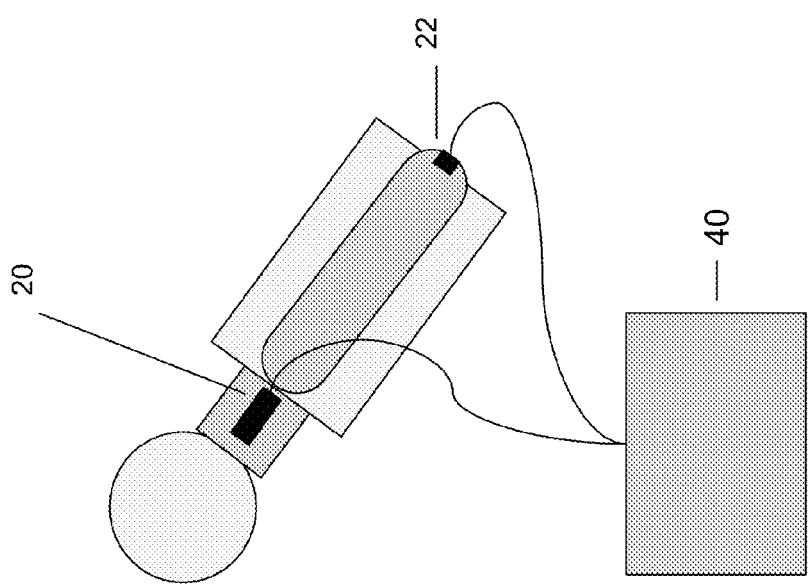
FIG. 6 illustrates the use of the system.

In addition to providing a method for determining cerebral tissue oxygenation in a patient, in another aspect of the invention, a system useful to determine cerebral tissue oxygenation in a patient is provided as illustrated in FIGS. 4-6. The system comprises a first module 20, for example comprising a device 100 or 200, useful to optically obtain jugular venous output signals against time from the patient at selected wavelengths of light, a second module 22 e.g. a pulse oximeter, useful to obtain cardiac arterial output signals at selected wavelengths of light, e.g. based on carotid arterial pulse, from the patient, and a signal processing module 40 which receives output signals from the first and second modules, separates the cardiac arterial output signals obtained at the selected wavelengths of light, e.g. first and second wavelengths of light, from the corresponding jugular venous output signals, e.g. first and second jugular venous output signals, to yield cerebral pulse output signals, e.g. first and second cerebral pulse output signals, and calculates cerebral tissue oxygenation therefrom. The signal processing module 40 may also be operable to digitize the output of each device into a visual output for presentation on a display unit, e.g. a monitor. Alternatively, the signal processing unit is adapted to calculate average cerebral tissue oxygenation based on the jugular venous output signals, cardiac arterial oxygenation based on the cardiac arterial output signals, and then provide an estimate of cerebral oxygenation consumption based on the difference of internal jugular venous oxygenation and cardiac arterial oxygenation.

The signal processing module 40 may include one or more microprocessors (e.g. digital signal processor, Texas Instruments) or digital acquisition boards to convert the analogue signal (e.g. current/voltage) received from the first and second modules to a digital signal and perform signal processing such as signal filtering using fourier transform, and a display unit, such as a monitor, which is in communication with or connected to the microprocessor(s) and functions to display one or more signals as a waveform through a user interface. The display may include a trend curve plot and an oxygenation value.

Alternatively, as will be understood by a person of skill in the art, the signal processing module 40 may be separate from the display unit 42, and in communication with an external display unit for presenting the output of the signal processing module thereon. For convenience, the monitor may be portable, and battery operated. According to another embodiment, the signal processing module may further comprise an algorithm processing unit 41 adapted to calculate cerebral tissue oxygenation as outlined based on determined cerebral venous output values.

Referring to FIG. 5, the signal processing module 40 can be implemented on one or more respective computing device(s) 101. The devices 101 in general can include a network connection interface 200, such as a network interface card or a modem, coupled via connection 218 to a device infrastructure 204. The connection interface 200 is connectable during operation of the device(s) 101 to a network 11 (e.g. an intranet and/or an extranet such as the Internet) which enables the device(s) 101 to communicate with each other as appropriate. The network 11 can, for example, support the communication of the output signal (e.g. current/voltage signal) provided by the photodetector 130/230 to the signal processing module 40.

The device(s) 101 may also have a user interface 202 coupled to the device infrastructure 204 by connection 222 to interact with a user. The user interface 202 can include one or more user input devices such as, but not limited to, a QWERTY keyboard, a keypad, a trackwheel, a stylus, a mouse, a microphone and a user output device such as an LCD screen display and/or a speaker. If the screen is touch sensitive, then the display can also be used as the user input device as controlled by the device infrastructure 204.

Operation of the device(s) 101 is facilitated by the device infrastructure 204. The device infrastructure 204 includes one or more computer processors 208 (e.g. a Digital Signal Processor) and can include an associated memory 210 (e.g. a random access memory). The computer processor 208 facilitates performance of the computing device 101 configured for the intended task through operation of the network interface 200, the user interface 202 and other application programs/hardware 207 of the computing device 101 by executing task-related instructions. These task-related instructions may be provided by an operating system and/or software applications 207 located in the memory 210, and/or by operability that is configured into the electronic/digital circuitry of the processor(s) 208 designed to perform the specific task(s). Further, it is recognized that the device infrastructure 204 may include a computer readable storage medium 212 coupled to the processor 208 for providing instructions to the processor 208. The computer readable medium 212 can include hardware and/or software such as, by way of example only, magnetic disks, magnetic tape, optically readable medium such as CD/DVD ROMS, and memory cards. In each case, the computer readable medium 212 may take the form of a small disk, floppy diskette, cassette, hard disk drive, solid-state memory card or RAM provided in the memory module 210. It should be noted that the above listed examples of computer readable media 212 may be used either alone or in combination. The device memory 210 and/or computer readable medium 212 may be used to store, for example, the desired output (e.g. pressure waveform) for use in processing of the signal received from the photodetector 130/230.

Further, it is recognized that the computing device(s) 101 may include executable applications 207 comprising code or machine readable instructions for implementing predetermined functions/operations including those of an operating system. The processor 208 as used herein is a configured device and/or set of machine-readable instructions for performing operations as described by example above. As used herein, the processor 208 may comprise any one or combination of, hardware, firmware, and/or software. The processor 208 acts upon information by manipulating, analyzing, modifying, converting or transmitting information for use by an executable procedure or an information device, and/or by routing the information with respect to an output device. The processor 208 may use or comprise the capabilities of a controller or microprocessor, for example. Accordingly, the functionality of the signal processing module 40 and/or the photodetector 130/230 may be implemented in hardware, software or a combination of both. Accordingly, the use of a processor 208 as a device and/or as a set of machine-readable instructions is hereafter referred to generically as a processor/module for the sake of simplicity.

It will be understood that the computing device(s) 101 may be, for example, personal computers, personal digital assistants, mobile phones, and content players. Further, it is recognised that each server computing device 101, although depicted as a single computer system, may be implemented as a network of computer processors, as desired.

Referring to FIG. 4, the signal processing module 40 may execute an algorithm (e.g. via the algorithm processing module 41) to translate the signals received by the photodetectors/pulse oximeter to a waveform. The waveform is the time varying component of the optical signal which can be translated into cerebral tissue oxygenation.

In use, a suitable patch probe of the first module of the system, comprising light source(s) and photodetectors, is generally placed on the neck of a patient at a site near the internal jugular vein. It is desirable for the patient to be lying down at about a 30 degree incline from the horizontal. The patient maintains regular breathing during the process of measuring the pulse of the blood vessel. Light from the light source is either reflected off of, or transmitted through, the target site on the patient's neck, and detected by the photodetector. The photodetector translates the detected light into an output signal (e.g. current/voltage) that may be digitized for expression as amplitude as a function of time to result in a jugular venous output signal (waveform). Simultaneously, a carotid artery output signal is obtained using the second module of the system, e.g. pulse oximeter. The output signals are received by the signal processing module to be processed, e.g. generation of cerebral pulse output signals, calculation of cerebral tissue oxygenation, digitization, and optionally display.

In another embodiment, a method and system for measuring local cerebral tissue oxygenation is provided. Such a method and system are useful to monitor cerebral blood oxygenation for early detection of localized cerebral tissue ischemic stroke.

The method comprises determining blood oxygenation measured from the external jugular vein (EJ), the internal jugular vein (IJ), cardiac artery (cardiac) and a cerebral site (measures oxygenation in scalp, skull and small portion of cerebral tissue). The external jugular vein contains, for the most part, venous blood from facial tissue (which is part of the scalp) flowing back to the heart, and thus, may be used to determine the venous oxygenation status of the scalp. The internal jugular vein contains venous blood from cerebral tissue/brain tissue flowing back to heart, and thus, may be used to determine the overall oxygenation status of cerebral tissues. The external and internal jugular veins are substantially parallel along the neck separated somewhat (e.g. by a few centimeters). The internal jugular vein is towards the front of neck and the external jugular vein is towards the ears. There are standard practices to visualize the internal and external jugular veins in order to determine blood oxygenation of these vessels. Blood oxygenation measured on a cerebral site, e.g. the head, provides the oxygenation of mixed vascular blood (vein and arterial) within the tissue underneath the site (e.g. mainly scalp, skull and a small portion of actual cerebral tissue). Blood oxygenation of the cardiac artery provides the arterial blood oxygenation value of the scalp, since arterial blood oxygenation is the same over the entire body.

Local cerebral tissue oxygenation (StO2) as obtained from a cerebral site as above may be expressed as the weighted average of scalp venous oxygenation (SvO2_scalp), scalp arterial oxygenation (SaO2_scalp) and cerebral tissue venous oxygenation (SvO2_cerebral) since the majority of blood vessels on the surface of brain are veins. This is summarized by the following equation:

$$StO2 = A \times SvO2\_scalp + B \times SvO2\_cerebral + C \times SaO2\_scalp \quad (6)$$

Parameters A, B, C are related to the spatial distribution and volume of corresponding blood vessels and the scattering and absorption properties of each of the tissues. Since scalp tissue is part of the facial tissue, SvO2_scalp, can be represented by SvO2_EJ (as above, the blood oxygenation obtained from the external jugular is facial venous oxygenation). The average cerebral venous oxygenation, SvO2_cerebral, can be represented by SvO2_IJ (as above), and SaO2_scalp can be represented by cardiac arterial oxygenation determined by pulse oximetry since arterial oxygenation is generally the same over the entire body. Thus, in view of the foregoing, equation (6) may be rewritten as:

$$StO2 = A \times SvO2\_EJ + B \times SvO2\_IJ + C \times SaO2 \quad (7)$$

Thus, the present method of monitoring local cerebral blood oxygenation in a patient comprises the steps of: determining the venous blood oxygenation from the scalp by generating at least first and second output signals of change in blood volume as current or voltage over time using at least one photodetector based on the reflection or transmission of at least first and second wavelengths of light from at least one light source, wherein the light is applied to the neck of the patient in the proximity of the external jugular vein; determining the average cerebral venous oxygenation by generating at least first and second output signals of change in blood volume as current or voltage over time using at least one photodetector based on the reflection or transmission of at least first and second wavelengths of light from at least one light source, wherein the light is applied to the neck of the patient in the proximity of the internal jugular vein; determining local blood oxygenation at one or more cerebral sites by generating at least first and second output signals of change in blood volume as current or voltage over time using at least one photodetector based on the reflection or transmission of at least first and second wavelengths of light from at least one light source, wherein the light is applied to the head of the patient in the proximity of the one or more cerebral sites; and determining cerebral arterial blood oxygenation by generating at least first and second cardiac arterial output signals as current or voltage of change in blood volume over time using a pulse oximeter for the first and second wavelengths of light; and comparing the local cerebral blood oxygenation to the average cerebral blood oxygenation, scalp venous blood oxygenation and scalp arterial oxygenation using a processor to identify changes in one or more of these to detect cerebral ischemia.

The conditions of this method of monitoring local cerebral blood oxygenation are similar to those used in a method for determining cerebral tissue oxygenation as described above. For example, the first and second wavelengths of light are each in the range of 400 nm to 1000 nm. Light transmission or reflection is detected in each case, and more than two wavelengths of light may be utilized which may provide a more accurate result, e.g. reduce error.

Thus, the present method is useful to monitor for and identify a change in cerebral tissue oxygenation. For example, ischemic stroke (in which there is a blockage of a cerebral vessel), can be detected by monitoring tissue oxygenation, local cerebral oxygenation (StO2), SvO2_EJ, SvO2_IJ (which is the average cerebral oxygenation, of the whole brain) and SaO2. If a drop or decrease in local cerebral oxygenation (StO2) occurs, but no change in SvO2_EJ, SvO2_IJ and SaO2, then a blockage of a local cerebral vessel has occurred. If there is a change in average cerebral oxygenation (SvO2_IJ), but not in local cerebral oxygenation (StO2), then there has also been a drop in cerebral oxygenation but it is in another part of the brain, and further probing at different cerebral sites can then be conducted to determine the location of the problem. In this regard, multiple cerebral sites may be simultaneously monitored in order to more readily identify the cerebral location of a drop in blood oxygenation, and thereby identify a cerebral site of ischemia. If there is a simultaneous change in local cerebral oxygenation (StO2), as well as in one of SvO2_EJ or SaO2, then the change in oxygenation has occurred in scalp venous or scalp arterial oxygenation, and is not as a result of a drop in cerebral oxygenation. Thus, simultaneously monitoring all four oxygenation measurements leads to a much more reliable determination of local cerebral tissue oxygenation.

Figure 9:
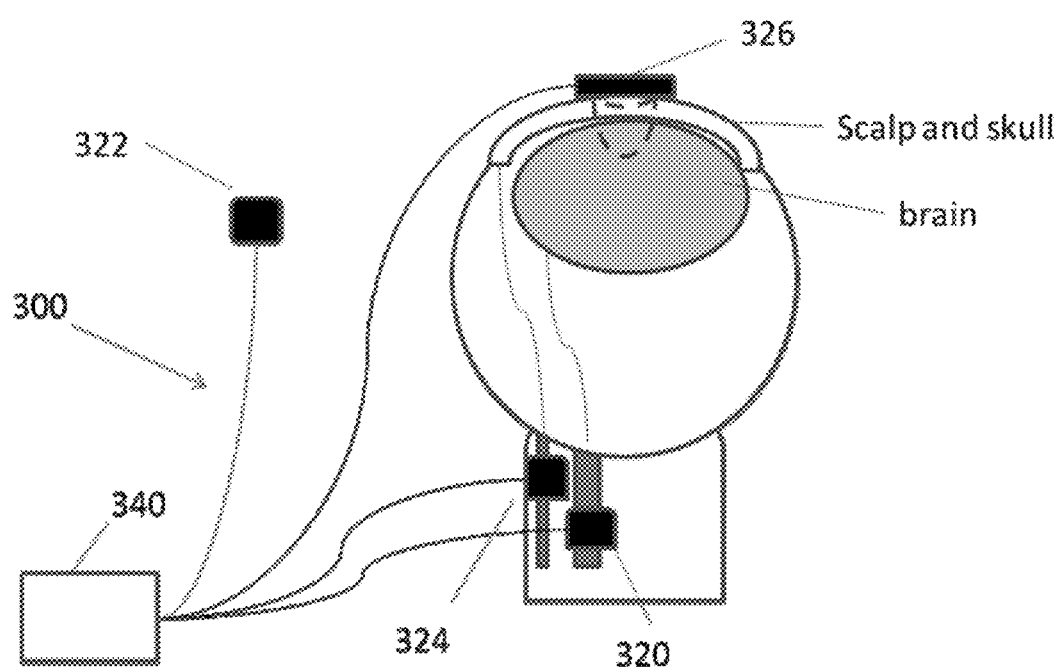
FIG. 9 illustrates an embodiment according to an aspect of the invention.

A system useful to monitor local cerebral tissue oxygenation in a patient is provided as illustrated in FIG. 9. The system 300 comprises a first module 320 to optically obtain internal jugular venous output signals against time from the patient at selected wavelengths of light to determine average cerebral blood oxygenation (SvO2_cerebral), a second module 322 e.g. a pulse oximeter, to obtain cardiac arterial output signals at selected wavelengths of light, e.g. based on carotid arterial pulse, from the patient to determine scalp arterial blood oxygenation (SaO2 scalp), a third module 324 to optically obtain external jugular venous output signals against time at selected wavelengths of light to determine venous scalp blood oxygenation (SvO2_scalp), a fourth cerebral module 326 to optically obtain output signals against time at a cerebral site (StO2), and a signal processing module 340 which receives output signals from the four modules, and calculates StO2, SvO2_scalp, SvO2_cerebral and SaO2_scalp for use in a method of monitoring local cerebral blood oxygenation as described.

Modules 320, 324 and 326 comprise at least one light source to emit light at one or more selected wavelengths of light, and at least one photodetector to receive transmitted or reflected light at each wavelenth and translate the received light into the output signal (change in blood volume), as current or voltage, over time. The arrangement of light source(s) and photodetector(s) in each module may be the same or different as shown in FIGS. 1-3.

In order to monitor cerebral blood oxygenation at more than one cerebral site, or at multiple cerebral sites, the system may comprise multiple cerebral modules 326 for placement at various sites on a patient head. In this way, a particular cerebral location of ischemia may be identified more readily. In particular, a drop or decrease in cerebral oxygenation (StO2) at one of the cerebral modules is indicative of a blockage of a local cerebral vessel at or near the cerebral site being monitored, and this would allow further analysis and any required immediate action to be taken in a specific manner. As one of skill in the art will appreciate, the signal processing module 340 may be adapted to receive output signals from one, two or multiple cerebral modules, and to calculate the blood oxygenation at each of these modules.

As described, the signal processing module 340 may include one or more microprocessors or digital acquisition boards to convert the analogue signal (e.g. current/voltage) received from each of the modules to a digital signal and perform signal processing such as signal filtering using fourier transform, and a display unit, such as a monitor, which is in communication with or connected to the microprocessor(s) and functions to display one or more signals in any desired format, e.g. waveform(s), oxygenation values, or any other format.

Embodiments of the present invention are described by reference to the following specific example which is not to be construed as limiting.

EXAMPLE 1

Measurement of Cerebral Oxygenation in a Patient

Figure 7:
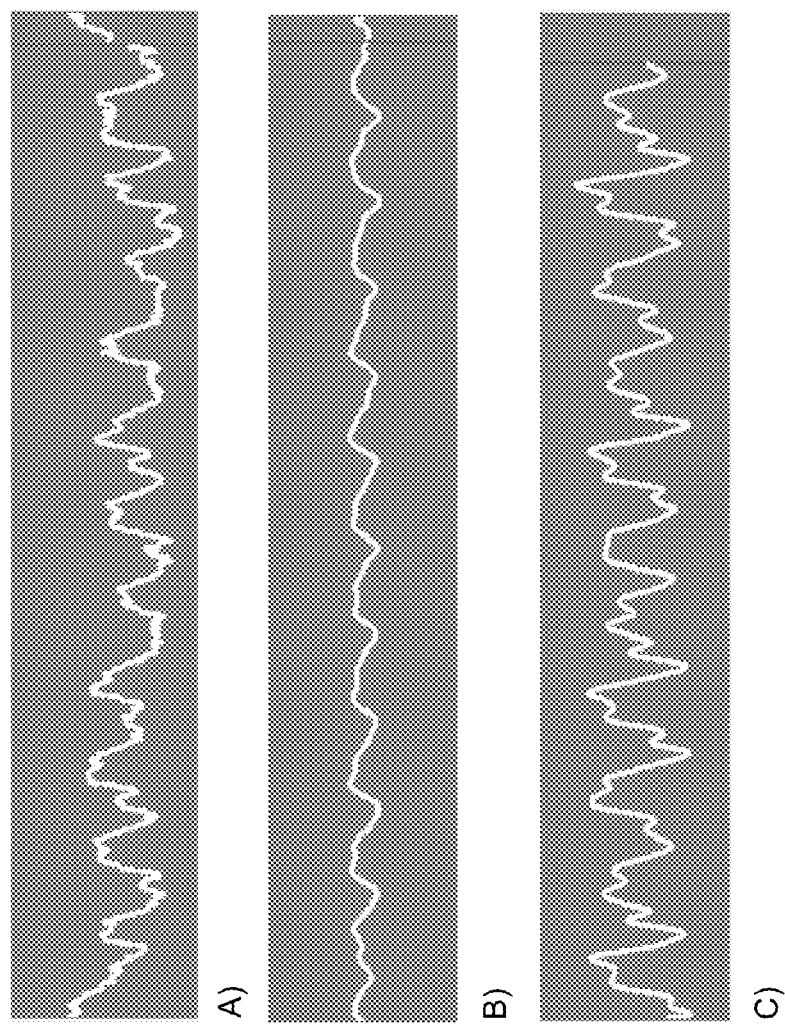
FIG. 7 illustrates waveforms obtainable from the system.
Figure 8:
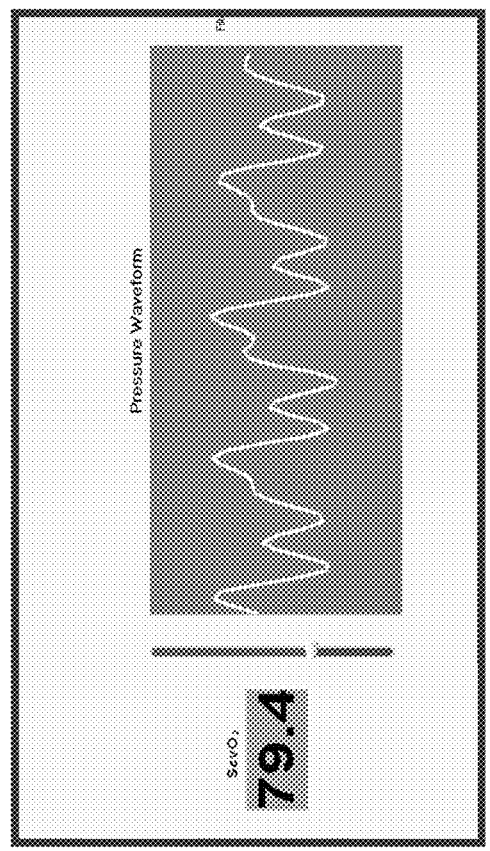
FIG. 8 visually illustrates results obtained using the present system and method.

The cerebral tissue oxygenation of a human subject was obtained using a system as shown in FIG. 6. The patient lay on a chair at about a 30 degree recline. The first module of the system, e.g. sensor patch, was placed on the neck of the patient at a site over the internal jugular vein. The second module (oximeter sensor patch) was placed on the index finger tip of the patient. While the patient maintained normal breathing, jugular venous pulse (output signal) was obtained from the first module and cardiac arterial pulse (output signal) was obtained from the second module. The signals were received by the signal processing module, processed as described above, to yield a jugular venous waveform (FIG. 7A), a cardiac arterial waveform (FIG. 7B) and a cerebral venous waveform (FIG. 7C). The amplitude of the detected signals is represented along the y-axis while the x-axis represents time. The signal processing module utilized this signal information to calculate cerebral oxygenation which can be displayed on a user-interface as a waveform and an oxygenation value as shown in FIG. 8.

I claim:

1. A system comprising:
   1) a first module for optically generating at least first and second internal jugular venous output signals as current or voltage based on change in blood volume over time at at least first and second wavelengths of light, wherein said first module comprises at least one light source to emit the light and at least one photodetector to receive transmitted or reflected light of each wavelength from the light source and translate it into the output signals;
   2) a second module comprising a pulse oximeter for generating at least first and second cardiac arterial output signals over time at the first and second wavelengths of light, respectively; and
   3) a signal processing means that functions to calculate average cerebral blood oxygenation based on the output signals from the first module, arterial blood oxygenation based on the output signals from the second module and cerebral tissue oxygenation based on the difference between average cerebral blood oxygenation and arterial blood oxygenation.

2. The system of claim 1, further comprising:
   a third module for optically generating at least first and second external jugular venous output signals as current or voltage based on change in blood volume over time at at least first and second wavelengths of light, wherein said third module comprises at least one light source to emit the light and at least one photodetector to receive transmitted or reflected light from the light source and translate it into the output signals; and
   at least one cerebral module for optically generating at least first and second cerebral site output signals as current or voltage based on change in blood volume over time at at least first and second wavelengths of light, wherein said cerebral module comprises at least one light source to emit the light and at least one photodetector to receive transmitted or reflected light from the light source and translate it into the output signals, wherein the signal processing means additionally functions to calculate scalp venous blood oxygenation based on the output signals from the third module and local cerebral blood oxygenation based on the output signals from the cerebral module.

3. The system of claim 2, comprising multiple cerebral modules, wherein said signal processing means functions to calculate local cerebral blood oxygenation for each of said modules based on output signals generated by said modules.

4. A system as defined in claim 2, wherein the first and second wavelengths of light are within the range of about 400-1000 nm.

5. A system as defined in claim 4, wherein the first wavelength is about 690 nm and the second wavelength is about 830 nm.

6. The system of claim 1, wherein the signal processing means is adapted to subtract arterial blood oxygenation from average cerebral blood oxygenation to yield a corrected cerebral tissue oxygenation value.

7. A system as defined in claim 1, wherein the first and second wavelengths of light are within the range of about 400-1000 nm.

8. A system as defined in claim 7, wherein the first wavelength is about 690 nm and the second wavelength is about 830 nm.

9. A system as defined in claim 7, wherein the signal processing means comprises one or more microprocessors and a display unit.

10. A system as defined in claim 1, wherein said first module comprises a light source to emit each wavelength of light and a photodetector for each light source.

11. The application has been amended as follows:
1) determining the average cerebral venous blood oxygenation in a patient using a processor based on at least first and second output signals of change in blood volume as current or voltage generated by at least one photodetector wherein said output signals are based on the reflection or transmission of at least first and second wavelengths of light from at least one light source, wherein the light is applied to the neck of the patient in the proximity of the internal jugular vein;
2) determining cerebral arterial blood oxygenation in the patient using a processor based on at least first and second cardiac arterial output signals over time generated using a pulse oximeter for the first and second wavelengths of light; and
3) calculating cerebral tissue oxygenation based on the difference between average cerebral venous blood oxygenation and cerebral arterial blood oxygenation.

12. The method of claim 11, additionally comprising the steps of:
determining scalp venous blood oxygenation in the patient using a processor by generating at least first and second output signals of change in blood volume as current or voltage over time using at least one photodetector, wherein the output signals are based on the reflection or transmission of at least first and second wavelengths of light from at least one light source, wherein the light is applied to the neck of the patient in the proximity of the external jugular vein;
determining local cerebral blood oxygenation at one or more cerebral sites in the patient using a processor by generating at least first and second output signals of change in blood volume as current or voltage over time using at least one photodetector, wherein the output signals are based on the reflection or transmission of at least first and second wavelengths of light from at least one light source, wherein the light is applied to the head of the patient in the proximity of the one or more cerebral sites;
and further comparing local cerebral blood oxygenation to the average cerebral venous blood oxygenation, scalp venous blood oxygenation and scalp arterial oxygenation using a processor to identify changes in one or more of these to identify cerebral ischemia.

* * * * *

UNITED STATES PATENT AND TRADEMARK OFFICE
CERTIFICATE OF CORRECTION

| | |
|---|---|
| PATENT NO. | : 8,788,005 B1 |
| APPLICATION NO. | : 13/913911 |
| DATED | : July 22, 2014 |
| INVENTOR(S) | : Xuefeng Cheng |

It is certified that error appears in the above-identified patent and that said Letters Patent is hereby corrected as shown below:

In The Claims

Column 13, line 37, in the preamble of claim 11, the phrase "The application has been amended as follows:" should read -- A method comprising the steps of: --

Signed and Sealed this
Thirtieth Day of December, 2014

Michelle K. Lee
*Deputy Director of the United States Patent and Trademark Office*